United States Patent [19]

Kuroda et al.

[11] Patent Number: 5,102,846
[45] Date of Patent: Apr. 7, 1992

[54] PROCESS FOR PREPARING CATALYSTS FOR PRODUCING METHACRYLIC ACID

[75] Inventors: Toru Kuroda; Motomu Oh-Kita, both of Otake; Kazuhiro Ishii, Toyama, all of Japan

[73] Assignee: Mitsubishi Rayon Co., Ltd., Tokyo, Japan

[21] Appl. No.: 598,305

[22] Filed: Oct. 16, 1990

[30] Foreign Application Priority Data

Oct. 25, 1989 [JP] Japan .................... 1-276085

[51] Int. Cl.$^5$ .................. B01J 23/72; B01J 27/18; B01J 27/19; B01J 27/198
[52] U.S. Cl. ..................... 502/205; 502/206; 502/209
[58] Field of Search .......... 502/209, 205, 206

[56] References Cited

U.S. PATENT DOCUMENTS

| | | | |
|---|---|---|---|
| 3,840,595 | 10/1974 | Grasselli et al. | 502/209 X |
| 3,925,464 | 12/1975 | Oda et al. | 502/209 X |
| 4,558,028 | 12/1985 | Tsuneki et al. | 502/209 X |

FOREIGN PATENT DOCUMENTS

| | | |
|---|---|---|
| 027351 | 4/1981 | European Pat. Off. |
| 2163567 | 7/1973 | France . |
| 2333770 | 7/1977 | France . |

OTHER PUBLICATIONS

Derwent Abstract, No. 85:096135 [16], of JP-A 60-044042, (ABEI).
Abstract: English Translation of Japanese Patent Kokai No. 60-239439 Dated: Nov. 28, 1985.
Abstract: English Translation of Japanese Patent Kokai No. 55-73347 Dated: Jun. 3, 1978.

*Primary Examiner*—W. J. Shine
*Attorney, Agent, or Firm*—Armstrong, Nikaido, Marmelstein, Kubovcik & Murray

[57] ABSTRACT

In a process for producing a catalyst having a composition represented by the following formula usable to produce methacrylic acid by the gas-phase catalytic oxidation of methacrolein with molecular oxygen, $$P_aMo_bCu_cV_dX_eY_fZ_gO_h$$

wherein P, Mo, Cu, V and O are phosphorus, molybdenum, copper, vanadium and oxygen, respectively, X is at least one element selected from the group consisting of arsenic, antimony, bismuth, germanium, zirconium, tellurium and silver, Y is at least one element selected from the group consisting of iron, zinc, chromium, magnesium, tantalum, manganese, barium, boron, gallium, cerium and lanthanum, Z is at least one element selected from the group consisting of potassium, rubidium, cesium and thallium, a, b, c, d, e, f, g and h are an atomic ratio of each element, and when b is 12, a is 0.5 to 3, c is 0.01 to 2, d is 0.01 to 3, e is 0.01 to 3, f is 0 to 3, g is 0.01 to 2 nd h is the number of oxygen atoms necessary to satisfy the valence of each component, an improvement comprising adding 0.05 to 1.0 mole of nitric acid based on 12 moles of a molybdenum atom to a slurry containing materials for the catalyst components. According to the present invention, a catalyst for gas-phase catalytic oxidation excellent in the conversion of methacrolein and selectivity for methacrylic acid is obtained.

2 Claims, No Drawings

PROCESS FOR PREPARING CATALYSTS FOR PRODUCING METHACRYLIC ACID

BACKGROUND OF THE INVENTION

1. Field of the Invention

The present invention relates to a process for preparing a catalyst used in producing methacrylic acid by the gas-phase catalytic oxidation of methacrolein.

2. Description of the Prior Art

Hitherto, a large number of proposals have been made in regard to a process for producing methacrylic acid by the gas-phase catalytic oxidation of methacrolein and a catalyst used therefor. For example, with the object of controlling micropores in the catalyst, it is proposed to use alcohols, nitrogen-containing heterocyclic compounds and other various compounds at the time of preparation of the catalyst (see for example Japanese Patent Application Kokai No. 60-239439 and No. 55-73347). However, these proposals have defects in that the results of reaction are not sufficient, the catalytic activity decreases significantly with the lapse of time and after-treatment is troublesome. At present, therefore, a further improvement in a process for preparing industrially usable catalysts is desired.

SUMMARY OF THE INVENTION

An object of the present invention is to provide a novel process for preparing a catalyst usable to advantageously produce methacrylic acid from methacrolein.

The present inventors have extensively studied to improve the conventional catalyst-preparation methods, and as a result, have found a novel process for preparing a catalyst which can produce methacrylic acid in higher yields than the catalysts prepared by the conventional methods.

DESCRIPTION OF PREFERRED EMBODIMENTS

In a process for producing a catalyst having a composition represented by the following formula usable to produce methacrylic acid by the gas-phase catalytic oxidation of methacrolein with molecular oxygen, $$P_a Mo_b Cu_c V_d X_e Y_f Z_g O_h$$

wherein P, Mo, Cu, V and O are phosphorus, molybdenum, copper, vanadium and oxygen, respectively, X is at least one element selected from the group consisting of arsenic, antimony, bismuth, germanium, zirconium, tellurium and silver, Y is at least one element selected from the group consisting of iron, zinc, chromium, magnesium, tantalum, manganese, barium, boron, gallium, cerium and lanthanum, Z is at least one element selected from the group consisting of potassium, rubidium, cesium and thallium, a, b, c, d, e, f, g and h are an atomic ratio of each element, and when b is 12, a is 0.5 to 3, c is 0.01 to 2, d is 0.01 to 3, e is 0.01 to 3, f is 0 to 3, g is 0.01 to 2 and h is the number of oxygen atoms necessary to satisfy the valence of each component. The present invention relates to an improvement comprising adding 0.05 to 1.0 mole, preferably 0.1 to 0.8 mole of nitric acid based on 12 moles of a molybdenum atom to a slurry containing materials for the catalyst components. Nitric acid referred to here means nitric acid added in producing the catalyst and excludes nitric acid radicals contained in the materials for the catalyst components.

What effect the addition of nitric acid gives to the catalyst is not strictly clear. However, from the fact that the diameter of micropores present at the catalyst surface shifts to a larger value in the range of about 500 Å to about 3000 Å by the addition of nitric acid, it may be considered that an ideal microporous structure for the oxidation of methacrolein to methacrylic acid is formed.

In the present invention, there is no need to limit the catalyst-manufacturing process to a special one, but any of the conventionally known various processes such as the vaporization-to-dryness process, precipitation process, oxide-mixing process, etc. may be used, so far as there is no large unbalance of the composition. The addition of nitric acid gives no difference in performance between the catalysts obtained whenever it is carried out in the course of mixing of materials for the catalyst components.

As materials used for preparation of the catalyst, the nitrate, carbonate, ammonium salt and halide of every component element can be used in proper combination. For example, as materials for the molybdenum component, ammonium paramolybdate, molybdenum trioxide, molybdenum chloride, etc. can be used. As materials for the vanadium component, ammonium metavanadate, vanadium pentoxide, vanadium chloride, etc. can be used.

The catalyst used in the process of the present invention can be used without a carrier, or supported on or diluted with an inert carrier such as silica, alumina, silica-alumina, silicon carbide, etc.

In producing methacrylic acid by the gas-phase catalytic oxidation with the catalyst obtained by the present invention, the methacrolein concentration of the gas used as a material can be changed in a wide range, but 1 to 20 vol.% is suitable, and particularly 3 to 10 vol.% is preferred. Methacrolein, a material, may contain small amounts of impurities such as water, a lower saturated aldehyde, etc. These impurities give substantially no effect to the reaction.

As an oxygen source for the gas-phase catalytic oxidation, to use air is economical, but air made rich in pure oxygen may be used if necessary. The oxygen concentration of the gas used as a material is determined by the molar ratio to methacrolein. The value of this molar ratio is 0.3 to 4, particularly preferably 0.4 to 2.5. The gas used as a material may be diluted with an inert gas such as nitrogen, steam, carbon dioxide gas, etc.

Reaction pressure used in producing methacrylic acid is preferably normal pressure to several atmospheric pressure. Reaction temperature can be selected from a range of 230° to 450° C., but a temperature of 250° to 400° C. is particularly preferred. This reaction can be carried out by using either a fixed bed or a fluidized bed.

The catalyst-preparation process of the present invention and examples of the reaction with the prepared catalyst are illustrated specifically below.

In the examples and comparative examples, the conversion of methacrolein and selectivity for produced methacrylic acid are defined as follows:

$$\text{Conversion of methacrolein (\%)} = \frac{\text{Number of moles of reacted methacrolein}}{\text{Number of moles of supplied methacrolein}} \times 100$$

$$\text{Selectivity for methacrylic acid (\%)} = \frac{\text{Number of moles of produced methacrylic acid}}{\text{Number of moles of reacted methacrolein}} \times 100$$

In the following examples and comparative examples, parts are by weight, and analyses were carried out by gas chromatography.

EXAMPLE 1

100 Parts of ammonium paramolybdate, 1.66 parts of ammonium metavanadate and 4.77 parts of potassium nitrate were dissolved in 300 parts of pure water. To the resulting solution were added a solution of 8.16 parts of 85% phosphoric acid in 10 parts of pure water and then 4.13 parts of antimony trioxide. The resulting mixture was heated to 95° C. with stirring.

Thereafter, a solution of 1.14 parts of copper nitrate in 30 parts of pure water and then 4.46 parts of 20% nitric acid were added, and the resulting mixed solution was evaporated to dryness while heating with stirring. The solid matter obtained was dried at 130° C. for 16 hours, shaped by applying pressure and heat-treated at 380° C. for 5 hours under air stream. The product obtained was used as the catalyst.

The composition of elements except oxygen of the catalyst obtained was $P_{1.5}Mo_{12}Cu_{0.1}V_{0.3}Sb_{0.6}K_1$ (catalysts described in the following examples also are represented by the composition of elements except oxygen). The amount of nitric acid added at the time of catalyst preparation was 0.3 mole per 12 moles of a molybdenum atom.

A tubular reactor was filled with this catalyst, and a mixed gas consisting of 5 vol.% of methacrolein, 10 vol.% of oxygen, 30 vol.% of steam and 55 vol.% of nitrogen was passed through the tubular reactor at a reaction temperature of 270° C. for a contact time of 3.6 seconds. The product was collected and analyzed by gas chromatography to find that the conversion of methacrolein was 80.2% and the selectivity for methacrylic acid was 82.3%.

In a micropore distribution range of 500 Å to 3000 Å, the maximum value of micropore diameter of this catalyst was about 1800 Å.

EXAMPLE 2

A catalyst having the same composition as in Example 1, $P_{1.5}mO_{12}Cu_{0.1}V_{0.3}Sb_{0.6}K_1$, was prepared according to Example 1 except that 20% nitric acid was added just before the addition of 85% phosphoric acid. Using this catalyst, the reaction for producing methacrylic acid was carried out under the same reaction conditions as in Example 1. As a result, it was found that the conversion of methacrolein wa 80.0% and selectivity for methacrylic acid was 82.5%.

EXAMPLE 3

A catalyst having the same composition as in Example 1, $P_{1.5}Mo_{12}Cu_{0.1}V_{0.3}Sb_{0.6}K_1$, was prepared according to Example 1 except that 20% nitric acid was added just before the addition of antimony trioxide. Using this catalyst, the reaction for producing methacrylic acid was carried out under the same reaction conditions as in Example 1. As a result, it was found that the conversion of methacrolein was 80.1% and selectivity for methacrylic acid was 82.3%.

EXAMPLE 4

A catalyst having the same composition as in Example 1, $P_{1.5}Mo_{12}Cu_{0.1}V_{0.3}Sb_{0.6}K_1$, was prepared according to Example 1 except that 1.49 parts of 60% nitric acid was added just before the addition of copper nitrate. Using this catalyst, the reaction for producing methacrylic acid was carried out under the same reaction conditions as in Example 1. As a result, it was found that the conversion of methacrolein was 80.2% and selectivity for methacrylic acid was 82.4%.

COMPARATIVE EXAMPLE 1

A catalyst having the same composition as in Example 1, $P_{1.5}Mo_{12}Cu_{0.1}V_{0.3}Sb_{0.6}K_1$, was prepared for comparison according to Example 1 except that 20% nitric acid was not added. Using this catalyst, the reaction for producing methacrylic acid was carried out under the same reaction conditions as in Example 1. As a result, it was found that the conversion of methacrolein was 80.4% and selectivity for methacrylic acid was 80.0%.

In a micropore distribution range of 500 Å to 3000 Å, the maximum value of micropore diameter of this catalyst was about 800 Å.

EXAMPLES 5 to 13

Catalysts shown in Table 1 were prepared according to Example 1. Using these catalysts, the reaction for producing methacrylic acid was carried out under the same conditions as in Example 1 except that reaction temperatures for producing methacrylic acid shown in Table 1 were used. The results are shown in Table 1.

COMPARATIVE EXAMPLES 2 to 10

Comparative catalysts shown in Table 1 were prepared according to Examples 5 to 13 except that 20% nitric acid was not added. Using these catalysts, the reaction for producing methacrylic acid was carried out under the same conditions as in Examples 5 to 13 to obtain results shown in Table 1.

TABLE 1

| | Composition of catalyst | Amount of nitric acid $HNO_3/Mo_{12}$ (mole/mole) | Reaction temperature (°C.) | Conversion of methacrolein (%) | Selectivity for methacrylic acid (%) |
|---|---|---|---|---|---|
| Example 5 | $P_{1.5}Mo_{12}Cu_{0.1}V_{0.8}Te_{0.2}Mg_{0.4}Fe_{0.2}Rb_1$ | 0.5 | 290 | 87.1 | 88.7 |
| Comparative Example 2 | | 0 | | 87.4 | 86.5 |
| Example 6 | $P_{1.5}Mo_{12}Cu_{0.1}V_{0.5}Bi_{0.2}Sb_{0.5}Ba_{0.1}Tl_{0.8}$ | 0.2 | 290 | 87.1 | 89.6 |
| Comparative Example 3 | | 0 | | 87.0 | 87.3 |
| Example 7 | $P_{1.4}Mo_{12}Cu_{0.1}V_{0.4}Ge_{0.3}Fe_{0.2}B_{0.3}K_{0.3}Rb_{0.6}$ | 0.4 | 290 | 88.2 | 88.4 |
| Comparative Example 4 | | 0 | | 87.8 | 86.7 |
| Example 8 | $P_{1.2}Mo_{12}Cu_{0.2}V_{0.5}Ag_{0.1}Ta_{0.3}Cs_1$ | 0.3 | 290 | 83.5 | 87.3 |

TABLE 1-continued

| | Composition of catalyst | Amount of nitric acid $HNO_3/Mo_{12}$ (mole/mole) | Reaction temperature (°C.) | Conversion of methacrolein (%) | Selectivity for methacrylic acid (%) |
|---|---|---|---|---|---|
| Comparative Example 5 | | 0 | | 83.6 | 85.0 |
| Example 9 | $P_2Mo_{12}Cu_{0.1}V_{0.6}Zr_{0.6}Cr_{0.2}Tl_{0.6}$ | 0.5 | 290 | 87.7 | 88.0 |
| Comparative Example 6 | | 0 | | 87.5 | 85.8 |
| Example 10 | $P_{1.5}Mo_{12}Cu_{0.2}V_{0.4}Ag_{0.1}Ge_{0.5}Ba_{0.2}Mn_{0.05}Cs_1$ | 0.2 | 290 | 86.3 | 88.2 |
| Comparative Example 7 | | 0 | | 86.2 | 87.3 |
| Example 11 | $P_{1.5}Mo_{12}Cu_{0.1}V_{0.5}As_{0.2}K_{0.8}Cs_{0.1}$ | 0.4 | 310 | 83.6 | 87.3 |
| Comparative Example 8 | | 0 | | 83.2 | 85.5 |
| Example 12 | $P_{1.5}Mo_{12}Cu_{0.2}V_{0.8}Sb_1Ga_{0.1}B_{0.3}Zn_{0.3}Ce_{0.1}K_1$ | 0.4 | 290 | 88.6 | 89.2 |
| Comparative Example 9 | | 0 | | 88.4 | 87.0 |
| Example 13 | $P_1Mo_{12}Cu_{0.2}V_{0.5}As_{0.1}Ce_{0.4}La_{0.2}K_{0.5}Cs_{0.5}$ | 0.6 | 270 | 90.1 | 89.8 |
| Comparative Example 10 | | 0 | | 90.2 | 87.5 |

What is claimed is:

1. In a process for producing a catalyst having a composition represented by the following formula usable to produce methacrylic acid by the gas-phase catalytic oxidation of methacrolein with molecular oxygen, $$P_aMo_bCu_cV_dX_eY_fZ_gO_h$$

wherein P, Mo, Cu, V and O are phosphorus, molybdenum, copper, vanadium and oxygen, respectively, X is at least one element selected from the group consisting of arsenic, antimony, bismuth, germanium, zirconium, tellurium and silver, Y is at least one element selected from the group consisting of iron, zinc, chromium, magnesium, tantalum, manganese, barium, boron, gallium, cerium and lanthanum, Z is at least one element selected from the group consisting of potassium, rubidium, cesium and thallium, a, b, c, d, e, f, g.and h are an atomic ratio of each element, and when b is 12, a is 0.5 to 3, c is 0.01 to 2, d is 0.01 to 3, e is 0.01 to 3, f is 0 to 3, g is 0.01 to 2 and h is the number of oxygen atoms necessary to satisfy the valence of each component, an improvement comprising adding 0.05 to 1.0 mole of nitric acid based on 12 moles of a molybdenum atom to a slurry containing materials for the catalyst components.

2. A process according to claim 1, wherein nitric acid is added to said slurry in an amount of 0.1 to 0.8 mole based on 12 moles of a molybdenum atom.

* * * * *